United States Patent [19] — Diana

[11] Patent Number: 5,051,437
[45] Date of Patent: Sep. 24, 1991

[54] THIAZOLYLPHENOXYALKYLISOX-AZOLES, RELATED COMPOUNDS, AND THEIR USE AS ANTIVIRAL AGENTS

[75] Inventor: Guy D. Diana, Stephentown, N.Y.

[73] Assignee: Sterling Drug Inc., New York, N.Y.

[21] Appl. No.: 395,837

[22] Filed: Aug. 18, 1989

[30] Foreign Application Priority Data

Jun. 24, 1986 [CA] Canada ................................. 512258

[51] Int. Cl.$^5$ ................. A07D 417/12; A01K 31/425
[52] U.S. Cl. ................................... 514/365; 548/146; 548/203; 548/204
[58] Field of Search ..................... 548/203, 204, 146; 514/365

[56] References Cited

U.S. PATENT DOCUMENTS 4,451,476 5/1984 Diana .................................. 424/272
4,857,539 8/1989 Diana et al. ......................... 514/378

FOREIGN PATENT DOCUMENTS 137242 4/1985 European Pat. Off. .
207453 1/1987 European Pat. Off. ............ 514/365

Primary Examiner—Robert Gerstl
Attorney, Agent, or Firm—Thomas L. Johnson; Frederik W. Stonner; Paul E. Dupont

[57] ABSTRACT

Compounds of the formula

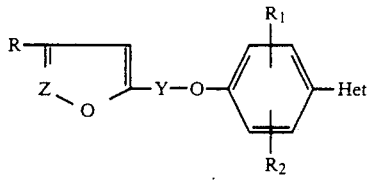

wherein:
Y is an alkylene bridge of 3-9 carbon atoms;
Z is N or HC;
R is hydrogen or lower-alkyl of 1-5 carbon atoms, with the proviso that when Z is N, R is lower-alkyl;
$R_1$ and $R_2$ are hydrogen, halogen, lower-alkyl, lower-alkoxy, nitro, lower-alkoxycarbonyl or trifluoromethyl; and
Het is selected from thiazole, benzothiazole and benzoxazole groups, are useful as antiviral agents, particularly against picornaviruses, including numerous strains of rhinovirus.

9 Claims, No Drawings

THIAZOLYLPHENOXYALKYLISOXAZOLES, RELATED COMPOUNDS, AND THEIR USE AS ANTIVIRAL AGENTS

BACKGROUND OF THE INVENTION a) Field of the Invention

This invention relates to novel heterocyclic substituted-phenoxyalkylisoxazoles and -furans, to methods for the preparation thereof, and compositions and methods for the use thereof as antiviral agents.

b) Information Disclosure Statement

Diana U.S. Pat. No. 4,451,476, issued May 29, 1984, discloses antivirally active compounds having the formula

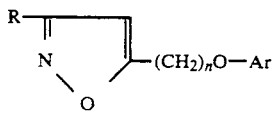

wherein:
R is alkyl of 1 to 3 carbon atoms;
n is an integer from 4 to 8; and
Ar is phenyl or phenyl substituted by one or two substituents selected from the group consisting of halogen, lower-alkyl, lower-alkoxy, nitro, cyano, carboxy, lower-alkoxycarbonyl, lower-alkanoyl, 1-oximino-lower-alkyl, hydrazinocarbonyl, carbamyl and N,N-di-lower-alkylcarbamyl.

Sterling Drug Inc. European Patent Application Publ. No. 137,242, published Apr. 17, 1985, discloses antivirally active compounds having the formula

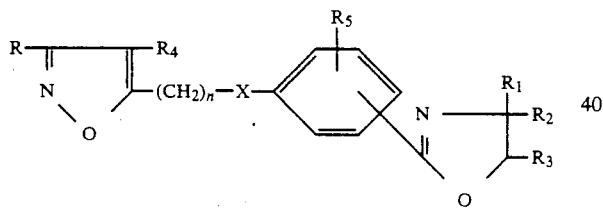

wherein:
R, $R_1$, $R_2$, $R_3$ and $R_4$ are each hydrogen or alkyl of 1 to 3 carbon atoms optionally substituted by hydroxy, lower-alkanoyloxy, lower-alkoxy, chloro, or N=Z, wherein N=Z is amino, lower-alkanoylamino, lower-alkylamino, di-lower-alkylamino, 1-pyrrolidinyl, 1-piperidinyl or 4-morpholinyl; with the proviso that R is other than hydrogen;
$R_5$ is hydrogen, lower-alkyl, halogen, nitro, lower-alkoxy, lower-alkylthio or trifluoromethyl;
X is O or a single bond; and
n is an integer from 3 to 9;
and to pharmaceutically acceptable acid-addition salts thereof.

SUMMARY OF THE INVENTION

It has now been found that compounds wherein the oxazoline ring of the compounds of the latter reference is replaced by selected other heterocycles are also effective antiviral agents.

Accordingly, the present invention relates to compounds of the formula

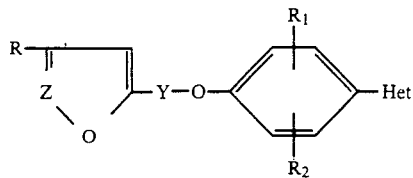

wherein:
Y is an alkylene bridge of 3–9 carbon atoms;
Z is N or HC;
R is hydrogen or lower-alkyl of 1–5 carbon atoms, with the proviso that when Z is N, R is lower-alkyl;
$R_1$ and $R_2$ are hydrogen, halogen, lower-alkyl, lower-alkoxy, nitro, lower-alkoxycarbonyl or trifluoromethyl; and
Het is selected from the group consisting of:

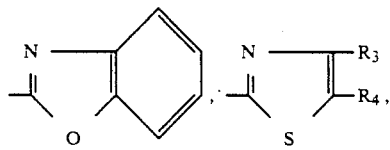

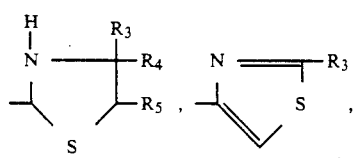

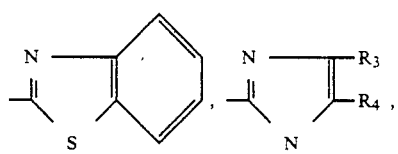

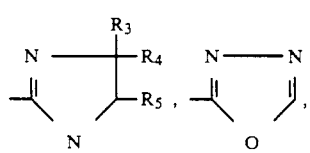

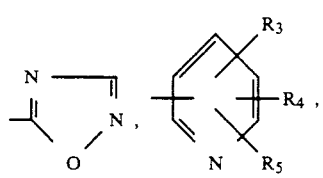

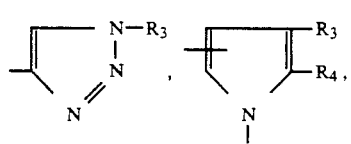

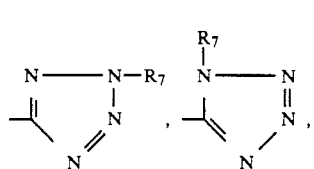

-continued

[structure: pyrazole with N-CH3 and methylene]

[structures: furan with R3, R6 and thiophene with R3, R6] and

[structure: dioxolane O—(CH2)n / O]

wherein
n is 2 or 3; and
R₃, R₄ and R₅ are hydrogen or lower-alkyl of 1–5 carbon atoms;
R₆ is hydrogen, lower-alkyl of 1–5 carbon atoms or chloro;
R₇ is hydrogen, or alkyl or hydroxyalkyl of 1–5 carbon atoms;
or pharmaceutically acceptable acid-addition salts of basic members thereof.

A preferred class of compounds within the scope of Formula I are those of the formula

[structure II: CH3-isoxazole-(CH2)5-O-phenyl(R1,R2)-Het]   II

The invention also relates to compositions for combating viruses comprising an antivirally effective amount of a compound of Formulas I or II in admixture with a suitable carrier or diluent, and to methods of combating viruses therewith, including the systemic treatment of viral infections in a mammalian host.

DETAILED DESCRIPTION INCLUSIVE OF PREFERRED EMBODIMENTS

The compounds of Formula I where Het is a nitrogen-containing heterocyclic group are sufficiently basic to form stable acid-addition salts with strong acids, and said salts are within the purview of the invention. The nature of the acid-addition salt is immaterial, provided it is derived from an acid the anion of which is essentially non-toxic to animal organisms. Examples of appropriate acid-addition salts include the hydrochloride, hydrobromide, sulfate, acid sulfate, maleate, citrate, tartrate, methanesulfonate, p-toluenesulfonate, dodecyl sulfate, cyclohexanesulfamate, and the like.

When the term halogen is used to define the substituents R₁ and R₂, any of the four common halogens, fluorine, chlorine, bromine or iodine are contemplated; and the term lower-alkoxycarbonyl refers to such groups having from two to four carbon atoms.

The compounds of Formula I can be prepared by a process which comprises reacting a compound of the formula

[structure III: R-Z-Y-Hal with O ring]   III wherein Hal is chlorine, bromine or iodine, with an alkali metal salt of a compound of the formula

[structure IV: HO-phenyl(R1,R2)-Het]   IV

The compounds of Formula I can also be prepared by an alternative process which comprises reacting a compound of the formula

[structure V: R-Z-Y-O-phenyl(R1,R2)-Hal']   V where Hal' is bromine or iodine, with a compound of the formula (R')₃Sn-Het'   VI where R' is lower-alkyl of 1–6 carbon atoms, and Het' is any of the aromatic type heterocyclic groups included in the definition of Het in Formula I; in the presence of a palladium complex catalyst.

The process for the preparation of compounds of Formula I by reacting intermediates of Formulas III and IV takes place by heating the reactants in an inert solvent in the presence of an alkali metal base, e.g. potassium carbonate or potassium hydroxide at a temperature between about 50° C. and 150° C.

The intermediates of Formula III where Z is N are prepared by reacting an alkali metal derivative of an isoxazole of the formula

[structure VII: R-N-O-CH3]   VII with a dihalide, Hal-Y'-Hal, where Y' is an alkylene bridge of 2 to 8 carbon atoms. Said alkali metal derivative is prepared in situ by treating the compound of Formula VII with an organo-alkali metal base under anhydrous conditions. Preferred organo-alkali metal bases are butyllithium and lithium diisopropylamide.

The intermediates of Formula III where Z is HC are prepared from the appropriate omega-(2-furan)alkanoic acid by reduction to the corresponding alcohol and replacement of the hydroxy group by halogen; or by direct alkylation of furan with a dihalide, Hal-Y-Hal, in the presence of a strong base such as butyllithium.

The intermediates of Formula IV are a generically known class of heterocyclic substituted phenols, prepared as described hereinafter in the general description and specific examples.

In the alternative process comprising reacting compounds of Formulas V and VI, the process is carried out using approximately equimolar amounts of the reactants in an inert solvent at a temperature between about 50° C. and 100° C., conveniently at the reflux temperature of the solvent. The reaction is complete in a period ranging from 5-24 hours. The palladium complex catalyst, present to the extent of about 5 mole percent, can be any such catalyst known to effect cross-coupling of organitin compounds with organic halides [cf. Kosugi et al., Bull. Chem. Soc. Japan 59, 677-679 (1986)], for example $PdCl_2(PPh_3)_2$, $Pd(PPh_3)_4$, $PdCl_2[P(o\text{-tolyl})_3]_2$, $PdCl_2+2P(OEt)_3$ and $PdCl_2(PhCN)_2$. A preferred catalyst is dichlorobis(triphenylphosphine)palladium $[PdCl_2(PPh_3)_2]$.

The intermediates of Formula V are prepared by reacting an alkali metal salt of a phenol of the formula

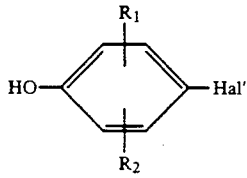

VIII with a compound of Formula III in a procedure analogous to that of the reaction of III with IV.

The organotin reagent of Formula VI is prepared by known procedures comprising reacting a tri-lower-alkyl-tin halide with an unsubstituted aromatic heterocycle in the presence of a strong base such as butyllithium under anhydrous conditions. The trialkyltin moiety enters the most reactive position on the heterocyclic ring; however, the trialkyltin moiety can be directed to other positions on the heterocyclic ring by using the appropriate halo-substituted heterocycle.

Certain compounds of the invention can be prepared by construction of the Het ring from intermediates having a cyano or formyl group on the phenyl ring, as follows.

The compounds of Formula I where Het is a 4,5-dihydro-1H-imidazolyl group:

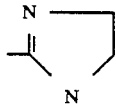

are prepared from the corresponding cyanophenyl compounds of the formula

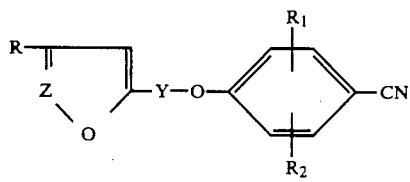

IX by heating the latter with ethylenediamine in acid medium. The compounds of Formula IX are in turn prepared from the appropriate cyanophenol and a compound of Formula III.

The compounds of Formula I where Het is a 2-thiazolyl group:

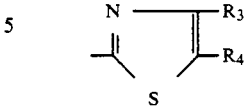

are prepared from the corresponding cyanophenyl compounds of Formula IX by conversion of the latter to the corresponding thioamide with hydrogen sulfide in pyridine, and then reacting the thioamide with a haloalkanone, $R_3CH(Hal)\text{—}CO\text{—}R_4$.

The compounds of Formula I where Het is a tetrazole group:

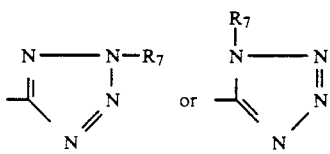

are prepared from the corresponding cyanophenyl compounds of Formula IX by reaction of the latter with sodium azide to give a tetrazole when $R_7$ is hydrogen. Treatment of the latter with a lower-alkyl halide or hydroxy-lower-alkyl halide in the presence of a base gives both isomeric tetrazoles where $R_7$ is lower-alkyl or hydroxy-lower-alkyl.

The compounds of Formula I where Het is a group of the formula

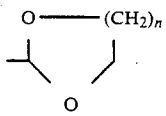

are prepared by conventional cyclic acetal formation by reacting a benzaldehyde derivative of the formula

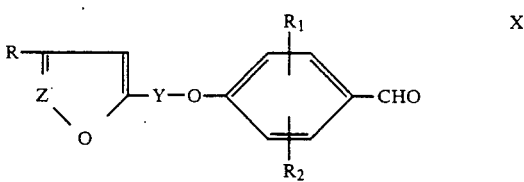

X with ethylene glycol or propylene glycol. The compounds of Formula X are in turn prepared by reacting the appropriate 4-hydroxybenzaldehyde with a compound of Formula III.

The compounds of Formula I where Het is a 2-thiazolidinyl group:

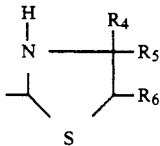

are prepared by reacting a benzaldehyde derivative of Formula X with an amino alkanethiol, $H_2N\text{—}C(R_4R_5)CH(R_6)\text{—}SH$, heated in a non-polar organic solvent with an acid catalyst.

The compounds of Formula I where Het is a 4-triazolyl group:

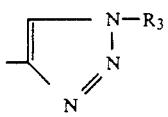

are prepared by reacting a cyanophenyl compound of the Formula IX with the lithium derivative of a N-nitrosoamine, $R_3(CH_3)N—N=O$ according to the procedure of Seebach et al., Angew. Chem., International Ed. 11, 1102 (1972).

The compounds of Formula I where Het is a 4,5-dihydro-3H-pyrrol-2-yl group:

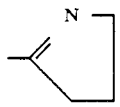

can be prepared by reacting a compound of Formula V with 1-trimethylsilylpyrrolidin-2-one according to the procedure described by Feringa and Jansen, Tetrahedron Letters 507 (1986).

The structures of the compounds of the invention were established by the modes of synthesis, by elementary analysis, and by infrared and nuclear magnetic resonance spectra.

The following examples will further illustrate the invention.

EXAMPLE 1

3-Methyl-5-{5-[4-(1,3,4-oxadiazol-2-yl)phenoxy]pentyl}-isoxazole [II; $R_1$ and $R_2$=H, Het=2-(1,3,4-oxadiazolyl)]

A mixture of 23.6 g 4-(1,3,4-oxadiazolyl)phenol (U.S. Pat. No. 4,218,458, Example XIX), 35 g 5-(5-bromopentyl)-3-methylisoxazole and 40 g milled potassium carbonate in 1.5 liters acetonitrile under nitrogen was heated to reflux. A catalytic amount of sodium iodide was added and refluxing continued for 4 hrs. The reaction mixture was filtered and concentrated to a solid residue. The latter was dissolved in ethyl acetate and the solution washed with water and saturated sodium chloride solution, dried over magnesium sulfate and concentrated in vacuo. The residue was recrystallized from triethylamine to give 18.5 g 3-methyl-5-{5-[4-(1,3,4-oxadiazol-2-yl)phenoxy]pentyl}isoxazole, white needles, m.p. 84°–86° C.

EXAMPLE 2 a) 2-(4-Methoxyphenyl)-4,5-dimethylthiazole

To a stirred mixture of 65.1 g (4-methoxy)thiobenzamide and 156 ml ethanol was added dropwise 50.1 g 3-chloro-2-butanone, and the reaction mixture was heated at reflux for 3 hours. An additional 6.1 g 2-chloro-3-butanone was added and heating was continued for an additional hour. The reaction mixture was cooled, 300 ml ether added, and the solid which precipitated was collected and dried to give 74.5 g 2-(4-methoxyphenyl)-4,5-dimethylthiazole in the form of its hydrochloride monohydrate, m.p. 166°–170° C.

b) 4(4,5-Dimethyl-2-thiazolyl) phenol [IV; $R_1$ and $R_2$=H, Het=(4,5-dimethyl-2-thiazolyl)]

The product of part (a) (70.7 g) was added to 470 g pyridine saturated with hydrogen chloride gas, and the mixture was heated 2 hours at reflux. The reaction mixture was poured into 3000 ml ice-water, made basic with ammonium hydroxide, and the solid product was collected. The latter was purified by recrystallization from toluene to give 38.8 g 4-(4,5-dimethyl-2-thiazolyl)phenol, m.p. 194°–195° C.

c)

3-Methyl-5-{5-[4(4,5-dimethyl-2-thiazolyl)phenoxy]pentyl}isoxazole [II; $R_1$ and $R_2$=H, Het=(4,5-dimethyl-2-thiazolyl)] was prepared from 2.0 g 4-(4,5-dimethyl-2-thiazolyl)phenol and 2.3 g 5-(5-bromopentyl)-3-methylisoxazole according to the procedure of Example 1: yield 2.5 g, m.p. 96°–97° C. (yellow to orange crystals from ethyl acetate).

EXAMPLE 3 a) 2-(4-Hydroxyphenyl)benzothiazole [IV; $R_1$ and $R_2$=H, Het=benzothiazol-2-yl]

A mixture of 3.7 g 2-aminophenol, 4.2 g 4-hydroxybenzoic acid, 4.5 g phosphorus pentoxide and 45 g methanesulfonic acid was stirred for one hour at room temperature and then heated at 90° C. for 10 hours. The reaction mixture was poured slowly into 750 ml 5% sodium bicarbonate solution. The solid which precipitated was collected and dried to give 7.0 g 2-(4-hydroxyphenyl)-benzothiazole.

b)

2-{4-[[5-(3-Methyl-5-isoxazolyl)pentyl]oxy]phenyl}benzothiazole [II; $R_1$ and $R_2$=H, Het=benzothiazol-2-yl] was prepared from 5 g 2-(4-hydroxyphenyl)benzothiazole and 5.1 g 5-(5-bromopentyl)-3-methylisoxazole according to the procedure of Example 1: yield 6.9 g, m.p. 120°–121° C. when recrystallized from triethylamine and then from isopropyl acetate.

EXAMPLE 4 a) 4-(2-Benzothiazolyl)-2-nitrophenol [IV; $R_1$=2-$NO_2$, $R_2$=H, Het=benzothiazol-2-yl]

A mixture of 14.8 g 2-aminothiophenol, 21.6 g 4-hydroxy-3-nitrobenzoic acid, 18 g phosphorus pentoxide and 180 g methanesulfonic acid was heated at 90° C. for 10 hours. The reaction mixture was brought to pH 5 by addition of sodium bicarbonate and sodium hydroxide solutions, and the solid product collected. The latter was recrystallized first from ethyl acetate and then from acetonitrile to give 6.5 g of the above-indicated product, orange-brown needles, m.p. 214°–215° C.

b)

5-{5-[4-(2-Benzothiazolyl)-2-nitrophenoxy]pentyl}-3-methylisoxazole [II; $R_1$=$NO_2$, $R_2$=H, Het=benzothiazol-2-yl] can be prepared by reacting 4-(2-benzothiazolyl)-2-nitrophenol with 5-(5-bromopentyl)-3-methylisoxazole in accordance with the procedure of Example 1.

EXAMPLE 5

5-{5-[4-(2-Benzoxazolyl)phenoxy]pentyl}-3-methylisoxazole [II; $R_1$ and $R_2$=H, Het=benzoxazol-2-yl] was prepared from 5 g 2-(4-hydroxyphenyl)benzoxazole (prepared by heating 4-hydroxybenzamide with 2-aminophenol) and 11.1 g 5-(5-bromopentyl)-3-methylisoxazole according to the procedure of Example 1. There was obtained 5.35 g of the above-indicated product, m.p. 96°-98° C. (from isopropyl acetate).

EXAMPLE 6 a) 5-[5-(4-Thiocarbamylphenoxy)pentyl]-3-methylisoxazole

Hydrogen sulfide gas was bubbled through a solution of 17.49 g 5-[5-(4-cyanophenoxy)pentyl]-3-methylisoxazole and 4.5 ml triethylamine in 105 ml pyridine for a two hour period. The reaction mixture was allowed to stand for 20 hours and the solvent was removed in vacuo. The residue was recrystallized from acetonitrile to give 10.2 g 5-[5-(4-thiocarbamylphenoxy)pentyl]-3-methylisoxazole as a yellow solid, m.p. 156°-158° C.

b) 3-Methyl-5-{5-[4-(2-thiazolyl)phenoxy]pentyl}isoxazole [I; Z=N, Het=4-(2-thiazolyl), R=CH$_3$, R$_1$ and R$_2$=H, Y=(CH$_2$)$_5$]

A suspension of 7.5 g 5-[5-(4-thiocarbamylphenoxy)pentyl]-3-methylisoxazole and 24.6 g chloroacetaldehyde (50% in water) in 150 ml absolute ethanol was refluxed for 3.5 hours. The reaction mixture was concentrated in vacuo and the residue recrystallized from ethyl acetate-hexane to give 4.5 g 3-methyl-5-{-5-[4-(2-thiazolyl)phenoxy]pentyl}isoxazole, m.p. 78°-80° C.

EXAMPLE 7 a) 5-[5-(2,6-Dichloro-4-cyanophenoxy)pentyl]-3-methylisoxazole [IX; Y=(CH$_2$)$_5$, Z=N, R=CH$_3$, R$_1$=2-Cl, R$_2$=6-Cl] was prepared from 13.4 g 3,5-dichloro-4-hydroxybenzonitrile, 23.2 g 5-(5-bromopentyl)-3-methylisoxazole, 20.7 g potassium carbonate and 15 g sodium iodide in 250 ml dimethylformamide, similar to the procedure of Example 1, and was obtained in the form of colorless crystals (11.6 g), m.p. 59°-60° C. (from tertiary-butyl methyl ether-hexane).

b) 5-[5-(2,6 -Dichloro-4-this carbamylphenoxy)pentyl]-3-methylisoxazole was prepared from 7.3 g 5-[5-(2,6-dichloro-4-cyanophenoxy)pentyl]-3methylisoxazole, hydrogen sulfide and 2 ml triethylamine in 100 ml pyridine according to the procedure of Example 6(a), and was obtained in the form of a yellow solid (8.0 g), m.p. 138°-140° C.

c) 5-{5-[2,6-Dichloro-4-(4,5-dimethyl-2-thiazolyl)phenoxy]pentyl}-3-methylisoxazole [II; R$_1$ and R$_2$=Cl, Het=4,5-dimethyl-2-thiazolyl]

A mixture of 3.6 g 5-[5-(2,6-dichloro-4-this carbamylphenoxy)pentyl]-3-methylisoxazole and 3.0 g 3-bromo-2-butanone in 50 ml absolute ethanol was heated at reflux for 6 hrs. The reaction mixture was concentrated in vacuo and the residue partitioned between ether and saturated sodium bicarbonate solution. From the ether layer was isolated an orange oil which after chromatography and recrystallizaiton from ether-hexane gave 5-{5-[2,6-dichloro-4-(4,5-dimethyl-2-thiazolyl)phenoxy]pentyl}-3-methylisoxazole as a colorless solid, m.p. 57°-58° C.

EXAMPLE 8 a) 4-[5-(3-Methyl-5-isoxazolyl)pentyloxy]benzaldehyde

A solution of 7.2 g 4-hydroxybenzaldehyde, 14.6 g 5-(5-bromopentyl)-3-methylisoxazole, 4 g potassium hydroxide in 100 ml acetonitrile was heated at reflux for 1.5 hours. The reaction mixture was cooled and filtered, the solvent removed, and the residue recrystallized from isopropyl acetate-hexane to give 10.8 g 4-[5(3-methyl-5-isoxazolyl)pentyloxy]benzaldehyde as a pale-yellow powder.

b) 3-Methyl-5-{5-[4-(2-thiazolidinyl)phenoxy]pentyl}isoxazole [II; Het=4-(2-thiazolidinyl), R=CH$_3$, R$_1$ and R$_2$=H]

A solution of 4.00 g of 4-[5-(3-methyl-5-isoxazolyl)pentyloxy]benzaldehyde (part a above), 1.22 g of 2-aminoethanethiol and a trace of p-toluenesulfonic acid in 30 ml of toluene was heated at reflux for 2 hours using a Dean-Stark trap. The product was isolated and recrystallized from isopropyl acetate-hexane to give 1.93 g of the above-indicated product, m.p. 82°-84° C.

EXAMPLE 9 a) 4-(2-Methyl-4-thiazolyl)phenol

To a stirred solution of 400 g of 4-acetoxy-α-bromoacetophenone in 900 ml of absolute ethanol was added over a 2 minute period 117 g of thioacetamide, and the reaction mixture was heated at reflux for 2 hours and stirred overnight at room temperature. The solid product was collected to give 360 g of the hydrobromide salt (m.p. 253°-257° C.) of the desired product. The latter was dissolved in aqueous methanol and treated with potassium hydroxide solution to produce 2.5 g of 4-(2-methyl-4-thiazolyl)phenol, m.p. 212°-214° C.

b) 3-Methyl-5-{7-[4-(2-methyl-4-thiazolyl)phenoxy]heptyl}isoxazole [I; Z=N, Het=4-(2-methyl-4-thiazolyl), R$_1$ and R$_2$=H, Y=(CH$_2$)$_7$] was prepared from 7.3 g of 4-(2-methyl-4-thiazolyl)phenol and 5-(7-bromoheptyl)-3-methylisoxazole according to the procedure of Example 1: yield 10.6 g, m.p. 100°-101° C.

Biological evaluation of compounds of Formulas I and II has shown that they possess antiviral activity. They are useful in inhibiting virus replication in vitro and are primarily active against picornaviruses, including enteroviruses, polioviruses, echovirus and coxsackie virus, and especially numerous strains of rhinoviruses. The in vitro testing of the compounds of the invention against picornaviruses showed that viral replication was inhibited at minimum inhibitory concentrations (MIC) ranging from about 0.01 to about 5 micrograms per milliliter.

The MIC values were determined by a standard plaque reduction assay as follows: HeLa (Ohio) cells in monolayers were infected at a concentration of virus to give approximately 80 plaques per monolayer in the virus control (no drug present). The compound to be tested was serially diluted and included in the agar-medium overlay and in some cases, during the adsorption period as well. The MIC was determined to be that concentration of compound which reduced the number of plaques by 50% with respect to the untreated virus control.

In the standard test procedure, the compounds were tested against a panel of fifteen human rhinovirus (HRV) serotypes, namely HRV-2, -1A, -1B, -6, -14, -21, -22, -15, -25, -30, -50, -67, -89, -86 and -41. The MIC value for each rhinovirus serotype was determined, and the efficacy of each compound was determined in terms of $MIC_{50}$ and $MIC_{80}$ values, which is the concentration of the compound required to inhibit 50% and 80%, respectively, of the tested serotypes.

The following Table gives the testing results with the compounds of the invention. For some of the compounds, the $MIC_{50}$ and $MIC_{80}$ values are based on the testing of fewer than 15 rhinovirus serotypes. In these cases the number of serotypes (N) is indicated in parentheses after the $MIC_{80}$ figure.

TABLE

| Example No. | MIC (Polio 2) | $MIC_{50}$ (Rhinovirus) | $MIC_{80}$ (N) (Rhinovirus) |
|---|---|---|---|
| 2(c) | 1.0 | 0.16 | 0.57 |
| 3(b) | IA | 1.12 | 27.1 (6) |
| 5 | 0.9 | 0.3 | 0.94 |
| 6(b) | 0.06 | 0.48 | 1.2 |
| 7(c) | IA | 0.23 | 0.91 |
| 8 | 2.24 | IA | IA (2) |
| 9(b) | 5.3 | 0.8 | 99(a) (6) |

IA = Inactive at dose levels tested
(a) = Inactive against more than 20% of the serotypes tested The antiviral compositions are formulated for use by preparing a dilute solution or suspension in a pharmaceutically acceptable aqueous, organic or aqueous-organic medium for topical or parenteral administration by intravenous or intramuscular injection, or for intranasal or ophthalmic application; or are prepared in tablet, capsule, or aqueous suspension form with conventional excipients for oral administration.

I claim:

1. A compound of the formula:

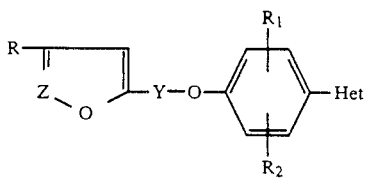

wherein:
Y is an alkylene bridge of 3-9 carbon atoms;
Z is N;
R is lower-alkyl of 1-5 carbon atoms;
$R_1$ and $R_2$ are hydrogen, halogen, lower-alkyl, lower-alkoxy, nitro, lower-alkoxycarbonyl or trifluoromethyl; and
Het is selected from the group consisting of:

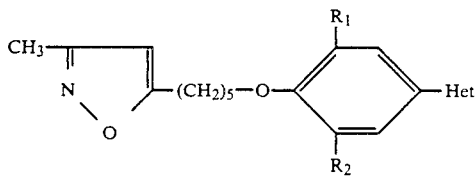

where $R_3$, $R_4$ and $R_5$ are hydrogen or lower-alkyl of 1-5 carbon atoms;
or pharmaceutically acceptable acid-addition salts thereof.

2. A compound according to claim 1 of the formula

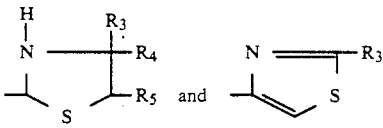

wherein $R_1$, $R_2$ and Het have the meanings given in claim 1.

3. 3-Methyl-5-{5[4-(2-thiazolidinyl)phenoxy]pentyl}-isoxazole, according to claim 2.

4. 3-Methyl-5-{7-[4(2-methyl-4-thiazolyl)phenoxy]heptyl}isoxazole, according to claim 1.

5. A composition for combating picornaviruses which comprises an antivirally effective amount of a compound according to claim 1, in admixture with a suitable carrier or diluent.

6. A composition according to claim 5 for combating rhinoviruses.

7. A method for combating picornaviruses which comprises contacting the locus of said viruses with an antivirally effective amount of a compound according to claim 1.

8. A method according to claim 7 for combating rhinoviruses.

9. A method for combating a picornaviral infection in a mammalian host which comprises administering to said host an antivirally effective amount of a compound according to claim 1.

* * * * *